United States Patent
Himmele et al.

[11] Patent Number: 5,212,183
[45] Date of Patent: May 18, 1993

[54] 4-(P-TERT.-BUTYLPHENYL)-3-METHYL-PIPERIDINES SUBSTITUTED AT THE NITROGEN, THEIR QUATERNARY SALTS AND THEIR USE AS FUNGICIDES

[75] Inventors: Walter Himmele, Walldorf; Ernst Buschmann, Ludwigshafen; Hubert Sauter, Mannheim; Ernst-Heinrich Pommer, Limburgerhof; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 641,818

[22] Filed: Jan. 16, 1991

Related U.S. Application Data

[63] Continuation of Ser. No. 248,260, Sep. 20, 1988, abandoned, which is a continuation of Ser. No. 797,882, Nov. 14, 1981, abandoned.

[30] Foreign Application Priority Data

Nov. 16, 1984 [DE] Fed. Rep. of Germany ....... 3441927

[51] Int. Cl.$^5$ .................. C07D 211/14; A01N 43/40
[52] U.S. Cl. .................... 514/317; 514/326; 546/192; 546/207; 546/236
[58] Field of Search ............ 546/192, 207, 236; 514/317, 326

[56] References Cited

U.S. PATENT DOCUMENTS

| | | | |
|---|---|---|---|
| 3,458,521 | 7/1969 | Jack et al. | 546/192 |
| 3,468,885 | 9/1969 | Sanne | 514/227 |
| 3,821,234 | 6/1974 | Koppe et al. | 546/192 |
| 4,188,396 | 2/1980 | Haas et al. | 546/192 |
| 4,202,894 | 5/1980 | Pfiffner | 546/192 |
| 4,241,058 | 12/1980 | Pfiffner | 546/192 |
| 4,284,635 | 8/1981 | Zimmerman | 546/192 |

Primary Examiner—Joseph Paul Brust
Assistant Examiner—Mary Susan H. Gabilan
Attorney, Agent, or Firm—Keil & Weinkauf

[57] ABSTRACT

Compounds of the formula I

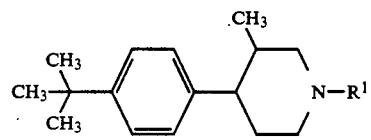

and of the formula II

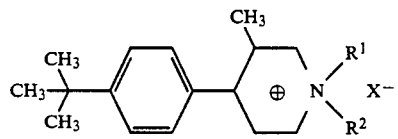

where $R^1$ is unsubstituted or substituted alkyl, unsubstituted or substituted alkenyl, or alkynyl, $R^2$ is alkyl or alkenyl and X is an acid radical, and the salts of the compounds of the formula I, and fungicides which contain these compounds.

5 Claims, No Drawings

4-(P-TERT.-BUTYLPHENYL)-3-METHYLPIPERIDINES SUBSTITUTED AT THE NITROGEN, THEIR QUATERNARY SALTS AND THEIR USE AS FUNGICIDES

This application is a continuation of application Ser. No. 07/248,260, filed on Sep. 20, 1988, now abandoned, which is a continuation of Ser. No. 06/797,882, filed on Nov. 14, 1981, now abandoned.

The present invention relates to useful novel piperidine derivatives which are substituted by p-tert.butylphenyl in the 4-position and by methyl in the 3-position and carry various radicals at the nitrogen, quaternary salts of these piperidines, and fungicides containing these. The novel compounds have an excellent fungicidal action and are useful for controlling fungi.

It is known that N-tridecyl-2,6-dimethylmorpholine (U.S. Pat. No. 3,468,885) can be used for controlling fungi, but its effect is unsatisfactory at low application rates.

We have found that piperidines which are substituted at the nitrogen, substituted in the 4-position by p-tert.-butylphenyl and substituted in the 3-position by methyl and are of the general formula

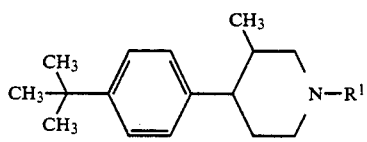
(I)

and the quaternary salts of these piperidines, of the general formula

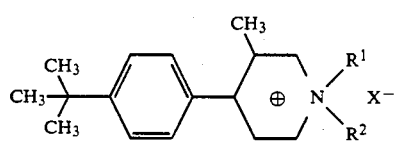
(II)

and the plant-tolerated tertiary salts of the piperidine compounds of the formula I have an excellent fungicidal action.

$R^1$ is alkyl of 1 to 10 carbon atoms (methyl, ethyl, propyl, butyl, pentyl or hexyl), alkenyl of 2 to 6 carbon atoms (allyl or methylallyl), alkynyl of 3 or 4 carbon atoms (propargyl), and the alkenyl radical may be substituted by phenyl or methoxyphenyl, 1, 2 or 3 carbon atoms in the alkyl radical may be replaced by —O— and the alkyl radical may be substituted by cycloalkyl of 5 to 7 carbon atoms (cyclohexyl), cycloalkenyl of 5 to 7 carbon atoms (cyclohexenyl), tetrahydropyran, dioxane, bicycloalkyl of 8 to 14 carbon atoms, tricycloalkyl of 8 to 14 carbon atoms, cycloalkoxy of 5 to 7 carbon atoms (cyclohexyloxy), phenyl or phenoxy, and the cyclic radicals in turn may be substituted by alkyl of 1 to 6 carbon atoms (methyl, ethyl, propyl or butyl), alkoxy of 1 to 4 carbon atoms (methoxy) or methylenedioxy, $R^2$ is alkyl of 1 to 4 carbon atoms (methyl, ethyl, propyl or butyl) or alkenyl of 2 to 4 carbon atoms (allyl or methylallyl), and X is a plant-tolerated acid radical. A subgenus of $R^2$ is methyl or allyl and a subgenus of $X^-$ is iodide or bromide.

$R^1$ and $R^2$ may be identical or different.

The fungicidal action of the novel compounds is governed by the structure of the piperidine compounds, so that the salts may contain any plant-tolerated acid radicals, for example radicals of the following acids: hydrochloric acid, hydrobromic acid, hydriodic acid, sulfuric acid, phosphoric acid, nitric acid, formic acid, acetic acid, propionic acid, benzenesulfonic acid, and dodecylbenzenesulfonic acid.

On the piperidine ring, the two substituents in the 3- and 4-positions can adopt a cis or trans configuration with respect to one another. The trans or cis form of the novel compounds can be obtained in pure form by fractionation of the piperidine compound unsubstituted at the nitrogen atom, followed by introduction of the radical at the nitrogen. The compounds contain two asymmetric carbon atoms, ie. carbon atoms 3 and 4 of the piperidine ring, and therefore occur in the form of their optical isomers and their enantiomer mixtures. The mixtures can be resolved into the individual isomers in a conventional manner. The present invention relates to the cis and trans isomers and the optical isomers of the novel compounds as well as mixtures of these.

The compounds of the formula I can be synthesized by condensing 4-tert.-butylbenzaldehyde with propionaldehyde to give 3-(4'-tert.-butylphenyl)-2-methylpropen-2-al (III) with the aid of a basic catalyst:

Stage 1

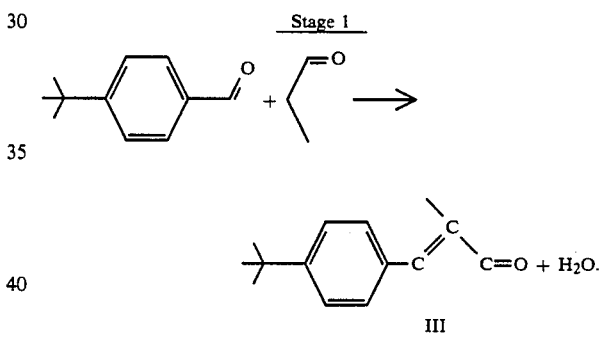

Compound III can be condensed with vinyl isobutyl ether (IV) to give 4-(tert.-butylphenyl)-3-methyl-6-isobutoxy-5,6-dihydropyran (V).

Stage 2

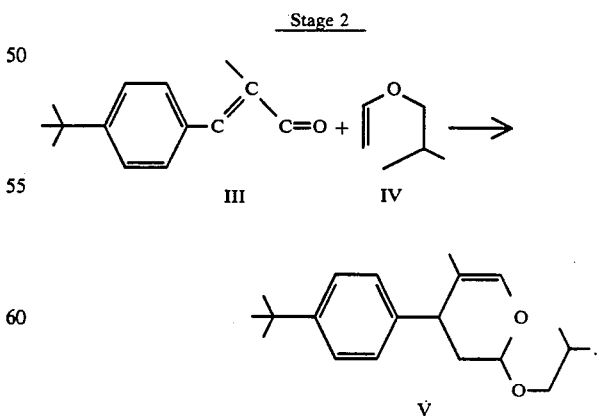

Compound V can be reacted with formic acid and water to give 2-methyl-3-(p-tert.-butylphenyl)-1,5-pentanedial (VI).

Stage 3

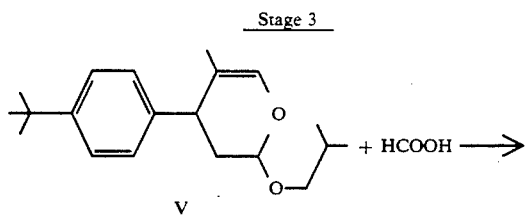

2-Methyl-3-(p-tert.-butylphenyl)-1,5-pentanedial (VI) can be hydrogenated with ammonia and hydrogen in the presence of a hydrogenation catalyst to give 4-(p-tert.-butylphenyl)-3-methylpiperidine (VII).

Stage 4

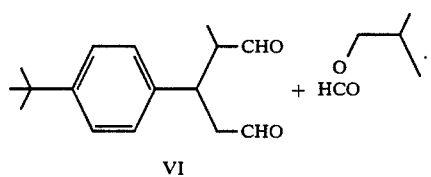

The radical $R^1$ may be introduced into the compound VII by means of a conventional method for alkylating secondary amines. The Leuckardt-Wallach method (Houben-Weyl, Methoden der organischen Chemie, volume 11/2, page 331, Georg Thieme Verlag Stuttgart, 1958) is particularly useful for this purpose.

The stated radicals $R^1$ may also be introduced by hydrogenating (for example with formic acid) an enamine (E) synthesized from the compound VII and an appropriate carbonyl compound.

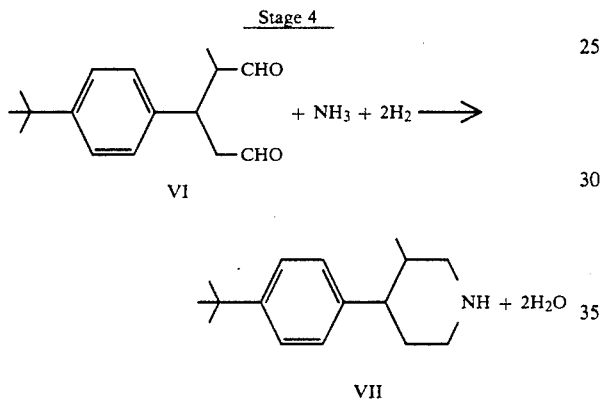

Compound VII can be purified by fractional distillation, the latter being carried out in such a way that it is possible to achieve substantial separation of the stereoisomeric forms attributable to the steric position of the two substituents in the 3- and 4-positions on the piperidine ring. The trans product VIIa generally boils at a lower temperature than the cis product (VIIb).

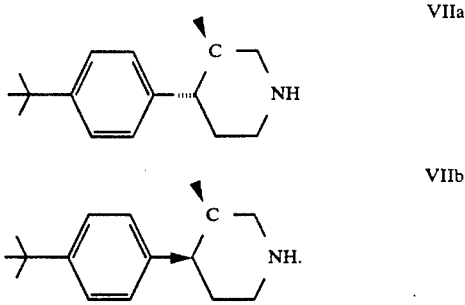

Under the preparation conditions described below, the trans form (VIIa) is predominantly formed (about 75%).

Another possible method of synthesizing compounds of the formulae I and II comprises reacting compound VI with an amine to give a 1,4-dihydropyridine VIII and then hydrogenating the latter to give a compound I.

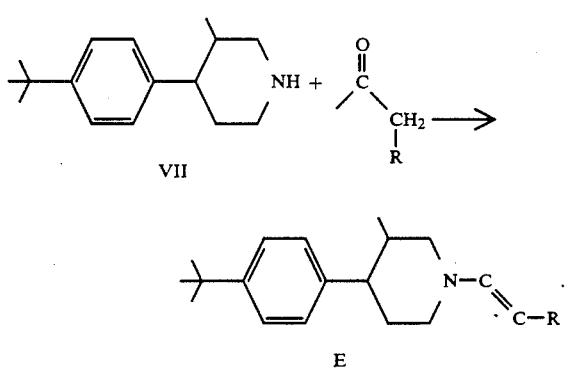

Purification of the compounds VIII prior to hydrogenation is advantageously omitted, and the hydrogenation is carried out using the crude condensate, in order to avoid losses through elimination of the radical $R^1$ with formation of the pyridine structure.

In most cases, the compounds of the formula I can be purified by a short path distillation. In the case of compounds of the formula I which contain a fairly bulky radical $R^1$ and are expected to have an excessively high boiling point, purification may also be effected via salt formation followed by liberation of the base.

The compounds of the formula I are generally viscous oils. In some cases, it is possible to obtain crystalline products. The compounds of the formula I are converted to the compounds of the formula II by reaction with a compound of the formula $R^2X$ in a conventional manner.

METHOD 1 for the synthesis of
4-(p-tert.-butylphenyl)-3-methyl-6-isobutoxy-5,6-dihydropyran (V)

3,000 g of 3-(4-tert.-butylphenyl)-2-methylprop-2-enal III and 2,000 g of vinyl isobutyl ether IV are introduced into a 10 l stirred autoclave, and 5 g of hydroquinone are added to the reaction mixture for stabilization. The autoclave is closed and then flushed with nitrogen, after which it is heated to 220° C., maintained under these conditions for 18 hours and then let down and opened. The reaction mixture (4,855 g) consists of about 39.6% of the desired product V. When the reaction mixture is worked up by fractionation in a laboratory column containing 10 sieve trays, a total of 1,379 g of the compound V of boiling point 135°-146° C. under 2 mbar are obtained from the 1,923 g shown to be present in the crude mixture by gas chromatographic analysis. This corresponds to a yield of 23%, based on the starting material III employed. 1,745 g of III, which contains some product V, are recovered. The last-mentioned amounts are reused for the reaction with vinyl isobutyl ether.

METHOD 2 for the synthesis of 3-(4'-tert.-butylphenyl)-2-methyl-1,5-pentanedial (VI)

600 g of formic acid and 600 g of water are initially taken in a 2 l stirred flask equipped with a thermometer, a means of effecting dropwise addition and a separating attachment for liquids. The mixture is heated to 100° C., and 1,200 g of product V are added dropwise in the course of 6 hours at this temperature. 277 g of isobutyl formate distil off. After a reaction time of a further 6 hours, another 134 g of isobutyl formate are obtained. 300 g of toluene are then added to the reaction mixture, and layer separation is allowed to take place. On standing overnight, a lower layer (890 g), which consists of water and formic acid, and an upper layer (1,415 g), which contains the product VI, are formed.

The organic phase is subjected to batchwise fractionation in a short path distillation apparatus, 712 g of product VI distilling over at from 150° to 165° C. under 0.2 mbar. This product is a slightly yellowish oil, which is stabilized by the addition of 356 g of tetrahydrofuran. The yield of product VI is 60%, based on product V employed.

METHOD 3 for the synthesis of 4-(4'-tert.-butylphenyl)-3-methylpiperidine (VII) by hydrogenation of product VI under aminating conditions 625 g of methanol together with 100 g of Raney cobalt are initially taken in a 5 l autoclave. The autoclave is closed so that it is pressure-tight, and is flushed with nitrogen. Thereafter, 500 g of liquid ammonia are injected, the autoclave is heated to 100° C. and a hydrogen pressure of 150 mbar is established. A mixture of 800 g of product VI and 270 g of tetrahydrofuran are injected into the autoclave in the course of 8 hours, and the injection line is flushed by subsequently forcing through 100 g of tetrahydrofuran. When the injection is complete, the reaction mixture is kept under the stated reaction conditions for a further 6 hours, while stirring. Hydrogen which has been consumed is replaced by injecting further hydrogen at intervals of 2 hours in order to maintain the hydrogen pressure.

Heating of the autoclave is then discontinued, and the autoclave is cooled to 60° C. and then let down carefully. During this procedure, unconsumed hydrogen as well as some of the ammonia escapes. The reaction mixture (2,112 g) can be removed from the autoclave after the latter has been let down, and is freed from the catalyst by filtration.

Methanol, tetrahydrofuran and the water formed during the reaction are distilled off under 50 mbar. Fractional distillation of the crude amine mixture gives 576 g of product VII having a boiling range of from 125° to 136° C. under 1 mbar. Gas chromatographic analysis shows that about 85% of the trans form (VIIa) and 15% of the cis form (VIIb) are present. The yield of VII is 77%, based on the product VI. Both the trans-rich fraction and the cis-rich fraction crystallize out partially when left to stand over a period of weeks.

EXAMPLE 1

Alkylation of 4-(4'-tert.-butylphenyl)-3-methylpiperidine. Synthesis of N-hexahydrobenzyl-4-(4'-tert.-butylphenyl)-3-methylpiperidine (IX) (compound No. 7 in Table 1)

30 g of 4-(4'-tert.-butylphenyl)-3-methylpiperidine (VII) were mixed with 17.5 g of hexahydrobenzaldehyde, the mixture was left to stand for 2 hours and 36 g of formic acid were then added. This reaction mixture was refluxed for 12 hours.

Fractionation by a short path distillation gave the following fractions:

| | | |
|---|---|---|
| 1 up to 185° C./5 mbar: | 4 g | According to gas chromatographic analysis, about 86% of compound IX |
| 2 up to 190° C./5 mbar: | 31 g | |
| Distillation residue | 4 g | |

The NMR and IR spectra confirm the presence of compound IX. The N-formyl product of VII is still present as an impurity.

EXAMPLE 2

Synthesis of 1-(3',5',5'-trimethylhex-1'-yl)-4-(4'-tert.-butylphenyl)-3-methylpiperidine (X) (compound No. 21 in Table 1)

28.9 g of VIIa were mixed with 23.7 g of 3,5,5-trimethylhexanal, the mixture warming up during this procedure. After two hours, 46 g of formic acid were added, and the resulting reaction mixture was refluxed for 12 hours. X was isolated by fractionation by a short path distillation. In addition to light ends and a small intermediate run of 5 g up to a pass-over temperature of 163° C./2 mbar, 41 g of product passed over at from 163° to 174° C./2 mbar. The distillation residue amounted to 4 g. According to gas chromatographic analysis, the main fraction (41 g) consisted of 89% of compound X. The NMR and IR spectra confirmed the presence of compound X.

EXAMPLE 3

Synthesis of 1-(3',5',5'-trimethylhex-1'-yl)-3-methyl-4-(4'-tert.-butylphenyl)-1-methylpiperidinium iodide (XI)

11 g of compound X were dissolved in 20 g of acetone, and 4 g of methyl iodide were added. The mixture warmed up slightly. After a few minutes, the quaternary piperidinium salt separated out as a finely crystalline powder. 8 g of compound XI with melting point 280° C. were obtained by filtration under suction and drying.

The NMR spectrum confirmed the presence of compound XI.

Table 1 lists the derivatives of 4-(4'-tert.-butyl-phenyl)-3-methylpiperidine (formula I) which are substituted at the nitrogen. These compounds were synthesized by the procedures stated under Examples 1 and 2.

Table 2 summarizes the compounds of the formula II. These compounds were obtained from compounds of the formula I by reaction with methyl iodide. The procedure followed was similar to that described in Example 3.

Table 3 lists substances of the formula II. These substances were obtained from compounds of the formula I by reaction with allyl bromide. The procedure described under Example 3 was followed.

TABLE 1

| Compound no. | $R^1$ (formula I) | Configuration in 3- and 4- position | Physical data b.p. in °C./mbar |
|---|---|---|---|
| 1 | n-propyl | — | — |
| 2 | i-propyl | — | — |
| 3 | n-butyl | — | — |
| 4 | 2-methyl-propyl | trans | 160–170/5 |
| 5 | 3-methyl-butyl | trans | 143–146/3 |
| 6 | benzyl | trans | 190–200/2 |
| 7 | hexahydrobenzyl | trans | 185–190/5 |
| 8 | methyl | 70% trans/30% cis | 118–130/0.2 |
| 9 | 4-methoxybenzyl | >95% trans | 186/2 |
| 10 | 3-(4-tert.-butylphenyl)-2-methyl-propyl | >95% trans | 225/2 |
| 11 | ethyl | — | — |
| 12 | 3-phenyl-2-propenyl | >95% trans | 220–230/2 |
| 13 | 2-ethyl-hexyl | >95% trans | 174–178/2 |
| 14 | 4-tert.-butyl-benzyl | >95% trans | 188/2 |
| 15 | 2-phenyl-propyl | >95% trans | 180/2 |
| 16 | 3-phenyl-butyl | >95% trans | 196/2 |
| 17 | 3-(4-methyl-3-cyclohexenyl)-butyl | >95% trans | 163/0.8 |
| 18 | (structure) | >95% trans | 160–162/1 |
| 19 | (4-methyl-tetrahydro-pyran-3-yl)-methyl | >95% trans | 167–172/1 |
| 20 | 5,5,3-trimethyl-hexyl | >90% cis | 172/1 |
| 21 | 5,5,3-trimethyl-hexyl | >96% trans | 174–176/2 |
| 22 | 4,4-dimethyl-pentyl | >96% trans | 154/1 |
| 23 | 4,4-dimethyl-pentyl | >90% cis | 178/3 |
| 24 | 2-(3,4-dimethoxy-phenyl)-butyl | >95% trans | 196–210/2 |
| 25 | (structure) | >95% trans | 190–194/1 |
| 26 | (structure) | >95% trans | 200–212/2 |
| 27 | 3-(4-tert.-butyl-cyclohexyl)-2-methyl-propyl | >95% trans | 222–224/2 |
| 28 | 2-phenyl-hexyl | >95% trans | 188–200/2 |
| 29 | (structure) | >95% trans | 210–215/2 |
| 30 | 2-phenoxy-propyl | >95% trans | 178–183/2 |
| 31 | 2-(3-methyl-phenoxy)-propyl | >95% trans | 210/2 |
| 32 | 2-(3-methyl-phenoxy)-propyl | >95% trans | 208–211/2 |
| 33 | 2-(4-methoxy-phenyl)-butyl | >95% trans | 212/1 |

TABLE 1-continued

| Compound no. | R¹ (formula I) | Configuration in 3- and 4-position | Physical data b.p. in °C./mbar |
|---|---|---|---|
| 34 | 2-phenyl-2-methyl-propyl | >95% trans | 166–170/1 |
| 35 | 3,3,2-trimethyl-butyl | 70% trans/30% cis | 142–150/1 |
| 36 | 2-(tetrahydropyran-4-yl)-ethyl | >95% trans | 196/2 |
| 37 | [structure: methylenedioxyphenyl-methylpropyl] | >95% trans | 197–218/2 |
| 38 | [structure: methylenedioxyphenyl-methylpropyl] | >95% cis | 220–226/2 |
| 39 | (tetrahydropyran-2-yl)-methyl | >98% trans | 174–184/2 |
| 40 | (tetrahydropyran-3-yl)-methyl | >98% trans | 200–220/ |
| 41 | (1,4-dioxan-2-yl)-methyl | >98% trans | 180–185/2 |
| 42 | 2-methyl-3,6-dioxa-octyl | >95% cis | 170–176/1 |

TABLE 2

| Compound no. | R² | R¹ | Configuration in 3- and 4-position | m.p. in °C. decomp. = decomposition | Anion |
|---|---|---|---|---|---|
| 43 | methyl | methyl | 65 trans/35 cis | 200–206 | iodide |
| 44 | methyl | 3-(4-tert.-butylphenyl)-2-methylpropyl | >95% trans | 236–237 | iodide |
| 45 | methyl | 3-(4-tert.-butylphenyl)-2-methylpropyl | >95% trans | 155–180 | bisulfate |
| 46 | methyl | 2-methyl-butyl | >95% trans | 223–232 | iodide |
| 47 | methyl | 2-methyl-propyl | >95% trans | 228–234 | iodide |
| 48 | methyl | 3-phenyl-2-propenyl | >95% trans | 186–188 | iodide |
| 49 | methyl | 2-ethyl-hexyl | >95% trans | 153–155 | iodide |
| 50 | methyl | 2-(4-methoxy-phenyl)-butyl | >95% trans | >260 | iodide |
| 51 | methyl | 2-phenyl-propyl | >95% trans | 280 decomp. | iodide |
| 52 | methyl | 5,5,3-trimethyl-hexyl | >95% trans | 250 decomp. | iodide |
| 53 | methyl | 4-tert.-butyl-benzyl | >95% trans | 224–230 | iodide |
| 54 | methyl | 3-phenyl-butyl | >95% trans | 157–172 | iodide |
| 55 | methyl | 2-phenyl-hexyl | >95% trans | 240–247 | iodide |
| 56 | methyl | 2-phenyl-2-methyl-hexyl | >95% trans | >260 decomp. | iodide |
| 57 | methyl | 5,5,3-trimethyl-hexyl | >90% cis | 250 decomp. | iodide |
| 58 | methyl | [structure: methylenedioxyphenyl with ethyl group] | >95% trans | >260 decomp. | iodide |
| 59 | methyl | 4,4-dimethyl-pentyl | >90% cis | 235–242 | iodide |
| 60 | methyl | 3-(4-tert.butyl-cyclohexyl)-2-methylpropyl | >95% trans | >260 decomp. | iodide |
| 61 | methyl | 2-phenoxy-propyl | >95% trans | 212–224 | iodide |
| 62 | methyl | [structure: bicyclic/adamantyl-type] | >95% trans | >260 decomp. | iodide |

TABLE 2-continued

| Compound no. | R² | R¹ | Configuration in 3- and 4- position | m.p. in °C. decomp. = decomposition | Anion |
|---|---|---|---|---|---|
| 63 | methyl | (norbornyl-methyl structure) | >95% trans | >260 decomp. | iodide |
| 64 | methyl | 5,5,3-trimethyl-hexyl | >95% trans | >260 decomp. | iodide |
| 65 | methyl | methyl | >95% trans | 228-233 | iodide |
| 66 | methyl | (C-O-phenyl-C structure) | >95% trans | >260 decomp. | iodide |
| 67 | methyl | 2-(4-tert.-butyl-phenoxy)-propyl | >95% trans | >260 decomp. | iodide |

TABLE 3

| Compound no. | R² | R¹ | Configuration in 3- and 4- position | m.p. in °C. decomp. = decomposition | Anion |
|---|---|---|---|---|---|
| 68 | allyl | methyl | 67% trans/33% cis | 198-212 | bromide |
| 69 | allyl | 3-methyl-butyl | > 95% trans | 229-231 | bromide |
| 70 | allyl | 2-methyl-propyl | > 95% trans | 225-229 | bromide |
| 71 | allyl | 3-phenyl-2-propenyl | > 95% trans | 146-150 | bromide |
| 72 | allyl | 5,5,3-trimethyl-hexyl | > 95% trans | 191-208 | bromide |
| 73 | allyl | 3-phenyl-butyl | > 95% trans | 196 | bromide |
| 74 | allyl | 2-phenyl-hexyl | > 95% trans | 180-187 | bromide |

The novel compounds have an excellent action on a broad spectrum of plant-pathogenic fungi, especially from the Ascomycetes and Basidiomycetes classes. Some of them have a systemic action and may be used as soil and foliar herbicides.

The fungicidal compounds are of particular interest for combatting a large number of fungi in various crops or their seed, especially wheat, rye, barley, oats, rice, Indian corn, cotton, soybeans, coffee, sugarcane, fruit, ornamentals in horticulture, and vegetables, such as cucumbers, beans and Cucurbitaceae.

The novel compounds are particularly suitable for combatting the following diseases: Erysiphe graminis in cereals, Erysiphe cichoracearum in Cucurbitaceae, Podosphaera leucotricha in apples, Uncinula necator in grapes, Puccinia species in cereals, Rhizoctonia solani in cotton, Ustilago species in cereals and sugarcane, Venturia inaequalis (scab) in apples, Septoria nodorum in wheat, Botrytis cinerea in strawberries and grapes, Cercospora musae in bananas, Pseudocercosporella herpotrichoides in wheat and barley, Pyricularia oryzae in rice, Hemileia vastatrix in coffee, Alternaria solani in potatoes and tomatoes, Plasmopara viticola in grapes, and Fusarium and Verticillium species in various plants.

The compounds are applied by spraying or dusting the plants with the active ingredients or treating seed with them. Application may be effected before or after infection of the plants or seed by the fungi.

The compounds according to the invention may be converted into the usual formulations, e.g. solutions, emulsions, suspensions, dusts, powders, pastes and granules. The application forms depend entirely on the purpose for which the compounds are being used; at all events they should ensure a fine and uniform distribution of the active ingredient. The formulations are prepared in conventional manner, e.g., by extending the active ingredient with solvents and/or carriers, if desired using emulsifiers and dispersants. Where water is used as diluent, other organic solvents may also be employed as auxiliary solvents. Suitable compounds for preparing such formulations are solvents such as aromatics (e.g., xylene, benzene),chlorinated aromatics (e.g., chlorobenzenes), paraffins (e.g., petroleum fractions), alcohols (e.g., methanol, butanol), ketones (e.g., cyclohexanone), amines (e.g., ethanolamine, dimethylformamide), and water; carriers such as natural rock flours (e.g., kaolins, diatomaceous earth, talc, chalk) and synthetic rock flours (e.g., highly disperse silicic acid, silicates); emulsifiers such as nonionic and anionic emulsifying agents (e.g. polyoxyethylene-fatty alcohol ethers, alkyl sulfonates and aryl sulfonates); and dispersants such as lignin, sulfite waste liquors and methyl cellulose.

The formulations generally contain from 0.1 to 95, and preferably from 0.5 to 90, wt % of active ingredient.

The application amounts depend on the type of effect desired, and vary from 0.02 to 3 kg/ha and more. The novel compounds may also be used for protecting materials, e.g., for combatting wood-destroying fungi such as Coniophora puteana and Polystictus versicolor. The novel active ingredients may also be employed as fungicidally effective components of oily wood preservatives for protecting wood against wood-discoloring fungi. The compounds are applied by treating, e.g., impregnating or painting, the wood with them.

The novel compounds also have a very good action on dermatophytes, especially Candida albicans.

The compounds may be applied either on their own or together with other, known, active ingredients, especially antibiotics.

The chemotherapeutic agents or formulations with conventional solid, semi-solid or liquid carriers or diluents and conventional pharmaceutical auxiliaries, depending on the desired administrative form and in a dose suitable for the administration, are prepared in conventional manner, especially by mixing (cf. H. Sucker et al., Pharmazeutische Technologie, Thieme-Verlag, Stuttgart, 1978).

Suitable administrative forms are, for example, tablets, dragees, capsules, pills, aqueous solutions, suspensions and emulsions, injectable solutions (sterile, if desired), non-aqueous emulsions, suspensions and solutions, ointments, creams, pastes, lotions, etc.

The concentration of the therapeutically active compound in the total pharmaceutical formulation is preferably from 0.5 to 90 wt %.

The formulations and the ready-to-use products made therefrom, e.g., solutions, emulsions, suspensions, powders, dusts, pastes or granules, are applied in known manner, for example by spraying, atomizing, dusting, scattering, seed-disinfecting or watering. Examples of formulations are given below.

I. 90 parts by weight of compound no. 4 is mixed with 10 parts by weight of N-methyl-alpha-pyrrolidone. A mixture is obtained which is suitable for application in the form of very fine drops.

II. 20 parts by weight of compound no. 19 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 21 is dissolved in a mixture consisting of 40 parts by weight of cyclohexanone, 30 parts by weight of isobutanol, and 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 36 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 69 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 70 is intimately mixed with 97 parts by weight of particulate kaolin. A dust is obtained containing 3% by weight of the active ingredient.

VII. 30 parts by weight of compound no. 19 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 6 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 7 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The novel active ingredients may also be mixed and applied with other active ingredients, e.g., herbicides, insecticides, growth regulators, other fungicides and fertilizers. When mixed with other fungicides, the spectrum of fungicidal action is in many cases increased.

The following list of fungicides with which the compounds according to the invention may be combined is intended to illustrate, and not restrict, the combination possibilities:

sulfur
dithiocarbamates and derivatives thereof, such as
ferric dimethyldithiocarbamate
zinc dimethyldithiocarbamate
zinc ethylenebisthiocarbamate
tetramethylthiuram disulfide
manganese ethylene bis-dithiocarbamate
manganese-zinc ethylenediamine-bisdithiocarbamate
ammonia complex of zinc-(N,N'-ethylene)-bisdithiocarbamate
and
N,N'-polyethylene-bis-(thiocarbamoyl)-disulfide
ammonia complex of zinc-(N,N'-propylene-bisdithiocarbamate)
and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'-dimethyl-N-phenylsulfuric acid diamide
5-ethoxy-3-trichloromethyl-1,2,3-thiadiazole
2-thiocyanomethylthiobenzthiazole
1,4-dichloro-2,5-dimethoxybenzole 4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiyne-4,4-dioxide
2,3-dihydro-5-carboxanilido-6-methyl-1,4-oxathiyne
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichlorethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazolylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorophenyl)-5-pyrimidinemethanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene
and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidine-2,4-dione
3-(3,5-dichlorophenyl)-1-isopropyl-carbamoylhydantoin
N-(3,5-dichlorophenyl)-1,2-dimethyl-cyclopropane-1,2-dicarboximide
2-cyano-N-(ethylaminocarbonyl)-2-methoximino)-acetamide
1-(2-(2,4-dichlorophenyl)-pentyl-1H-1,2,4-triazole
2,3-difluoro-alpha-(1H-1,2,4-triazolyl-1-ylmethyl)-benzhydryl alcohol.

For the following experiments, the prior art active ingredients N-tridecyl-2,6-dimethylmorpholine (A) and its acetate (B) were employed for comparison purposes.

APPLICATION EXAMPLE 1

Action on wheat mildew

Leaves of pot-grown wheat seedlings of the "Frühgold" variety were sprayed with aqueous liquors, the solids of which consisted of 80% (by weight) of active ingredient and 20% of emulsifier, and dusted, 24 hours after the sprayed-on layer had dried, with spores of wheat mildew (Erysiphe graminis var. tritici). The plants were then placed in a greenhouse at 20° to 22° C. and 75 to 80% relative humidity. The extent of mildew spread was determined after 7 days.

The results show that for example active ingredients 4, 19, 21, 36, 69 and 70, applied as 0.025% sprays had a better fungicidal action (e.g.,97%) than active ingredients A and B (90%).

APPLICATION EXAMPLE 2

Action on cucumber mildew

The leaves of pot-grown cucumber seedlings of the "Chinesische Schlange" variety were sprayed at the 2-leaf stage with a spore suspension of cucumber mildew (Erysiphe cichoracearum). After about 20 hours, the plants were sprayed to runoff with aqueous emulsions consisting (dry basis) of 80% of active ingredient and 20% of emulsifier. After the sprayed-on layer had dried, the plants were set up in the greenhouse at from 20° to 22° C. and a relative humidity of 70 to 80%. To assess the action of the novel compounds, the extent of fungus spread was determined after 21 days.

The results of this experiment show that for instance novel active ingredients 4, 6, 7, 9, 12, 13, 14, 15, 16, 19, 22, 23, 25, 30, 33, 36, 38, 46, 47, 48, 49, 52, 57, 59, 69, 70 and 71, applied as 0.025%. sprays, had a better fungicidal action (e.g., 97%) than active ingredient A (60%).

APPLICATION EXAMPLE 3

Action on leaf rust of wheat

Leaves of pot-grown wheat seedlings of the "Frühgold" variety were dusted with spores of rust (Puccinia recondita). The pots were then placed in a high humidity (90-95%) chamber at from 20° to 22° C. for 24 hours. During this time, the spores germinated and the germ tubes penetrated into the leaf tissue. The infected plants were then sprayed to run-off with aqueous liquors, the solids comprising 80% of active ingredient and 20% of emulsifier. After the spray coating had dried, the test plants were set up in a greenhouse at from 20° to 22° C. and from 65 to 70% relative humidity. After 8 days, the degree of development of the rust fungi on the leaves was determined.

The results of this experiment show that novel active ingredients 4, 5, 6, 7, 15, 19, 20, 23, 36, 47 and 70, applied as 0.025% sprays, had a better fungicidal action (e.g., 97%) than active ingredients A and B (50%).

APPLICATION EXAMPLE 4

Action on Botrytis cinerea in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus Botrytis cinerea, and placed at 22° to 24° C. in a chamber of high humidity. After 5 days, the disease had spread to such a great extent on the untreated plants that the necroses covered the major portion of the leaves.

The results of this experiment show that novel active ingredients 4, 6, 15, 16, 18, 25, 26, 29, 38, 44, 45, 48, 52, 53, 56, 57, 60, 62, 63, 66, 67, 72 and 74, applied as 0.05% sprays, had a better fungicidal action (e.g., 97%) than active ingredient A (70%).

APPLICATION EXAMPLE 5

Action on Candida albicans 0.1 ml of a germ suspension of Candida albicans in a casein peptone/soybean meal peptone solution was thoroughly mixed with aqueous dilutions of the candidate active ingredients. After 10 minutes, 1 ml was removed from the active ingredient/germ mixtures and added to 9 ml of inactivation liquid (0.1% of tryptone +0.85% of sodium chloride in twice-distilled water +3% of Tween 80+0.3% of lecithin+0.1% of cysteine). After 30 minutes' contact in the inactivation liquid, samples of casein peptone/soybean meal peptone agar were transferred to Petri dishes. The dishes were incubated for 72 hours at 37° C., and the concentration was determined at which there was no longer any fungus growth, i.e., the concentration at which the fungus was killed. Active ingredients 60 and 66 killed the fungus at a concentration of 6 ppm.

We claim:

1. A piperidine derivative of the formula

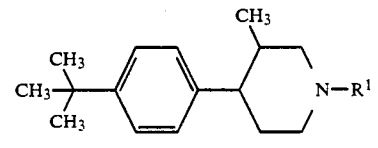

I

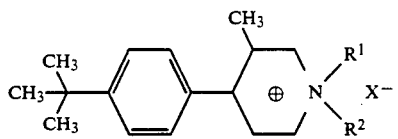

II in which $R^1$ is an alkyl of 1 to 10 carbon atoms in which 1, 2 or 3 of the carbon atoms may be replaced by —O—, said alkyl being substituted by cycloalkyl of 5 to 7 carbon atoms, cycloalkenyl of 5 to 7 carbon atoms, tetrahydropyran, dioxane, bicycloalkyl of 8 to 14 carbon atoms, tricycloalkyl of 8 to 14 carbon atoms, cycloalkoxy of 5 to 7 carbon atoms, phenyl or phenoxy, and the cyclic radicals in turn may be substituted by alkyl of 1 to 6 carbon atoms, alkoxy of 1 to 4 carbon atoms or methylenedioxy; and alkenyl of 2 to 6 carbon atoms which may be substituted by phenyl or methoxyphenyl; or an alkynyl of 3 or 4 carbon atoms, $R^2$ is alkyl of 1 to 4 carbon atoms or alkenyl of 2 to 4 carbon atoms, and X is a plant-tolerated anion of an acid chosen from the group consisting of hydrochloric acid, hydrobromic acid, formic acid, acetic acid, propionic acid, benzenesulfonic acid and dodecylbenzenesulfonic acid, or the plant-tolerated acid addition a salt of the piperidine derivative of the formula I with an acid selected from the group consisting of hydrochloric acid, hydroiodic acid, sulfuric acid, phosphoric acid, nitric acid, formic acid, acetic acid, propionic acid, benzenesulfonic acid and dodecylbenzenesulfonic acid.

2. A piperidine derivative of the formula

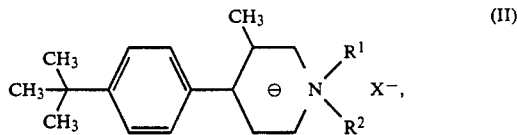

where $R^1$ is alkyl of 1 to 10 carbon atoms, alkenyl of 2 to 6 carbon atoms or alkynyl of 3 or 4 carbon atoms, and the alkenyl radical may be substituted by phenyl or methoxyphenyl, 1, 2 or 3 carbon atoms in the alkyl radical may be replaced by —O— and the alkyl radical may be substituted by cycloalkyl of 5 to 7 carbon atoms, cycloalkenyl of 5 to 7 carbon atoms, tetrahydropyran, dioxane, bicycloalkyl of 8 to 14 carbon atoms, tricycloalkyl of 8 to 14 carbon atoms, cycloalkoxy of 5 to 7 carbon atoms, phenyl or phenoxy, and the cyclic radicals in turn may be substituted by alkyl of 1 to 6 carbon atoms, alkoxy of 1 to 4 carbon atoms or methylenedioxy, $R^2$ is methyl or allyl and $X^-$ is iodide or bromide.

3. The piperidine derivative of claim 1, wherein $R^1$ is 5,5,3-trimethyl-hexyl.

4. The piperidine derivative of claim 1, wherein $R^1$ is hexahydrobenzyl.

5. A process for combatting fungi, wherein the fungi, or the materials, plants, seeds or soil threatened by fungus attack are treated with an effective amount of a piperidine derivative of the formula

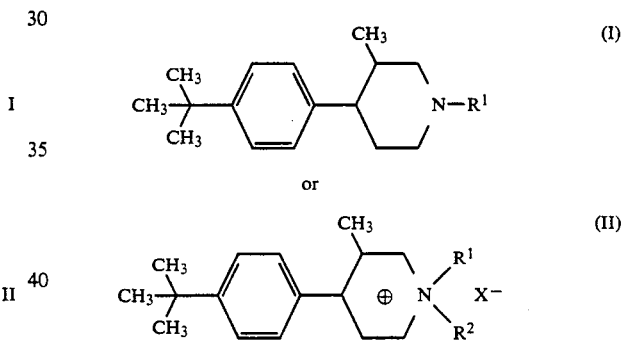

where $R^1$ is alkyl of 1 to 10 carbon atoms, alkenyl of 2 to 6 carbon atoms or alkynyl of 3 or 4 carbon atoms, and the alkenyl radical may be substituted by phenyl or methoxyphenyl, 1, 2 or 3 carbon atoms in the alkyl radical may be replaced by —O— and the alkyl radical maybe substituted by cycloalkyl of 5 to 7 carbon atoms, cycloalkenyl of 5 to 7 carbon atoms, tetrahydropyran, dioxane, bicycloalkyl of 8 to 14 carbon atoms, tricycloalkyl of 8 to 14 carbon atoms, cycloalkoxy of 5 to 7 carbon atoms, phenyl or phenoxy, and the cyclic radicals in turn may be substituted by alkyl of 1 to 6 carbon atoms, alkoxy of 1 to 4 carbon atoms or methylenedioxy, $R^2$ is alkyl of 1 to 4 carbon atoms or alkenyl of 2 to 4 carbon atoms, and X is a plant-tolerated anion of an acid chosen from the group consisting of hydrochloric acid, hydrobromic acid, hydriodic acid, sulfuric acid, phosphoric acid, nitric acid, formic acid, acetic acid, propionic acid, benzenesulfonic acid and dodecylbenzenesulfonic acid, or the plant-tolerated acid addition salt of the piperidine derivative of the formula I with an acid selected from the group consisting of hydrochloric acid, hydrobromic acid, hydriodic acid, sulfuric acid, phosphoric acid, nitric acid, formic acid, acetic acid, propionic acid, benzenesulfonic acid and dodecylbenzenesulfonic acid.

* * * * *

UNITED STATES PATENT AND TRADEMARK OFFICE
CERTIFICATE OF CORRECTION

PATENT NO. : 5,212,183

DATED : May 18, 1993

INVENTOR(S) : HIMMELE et al.

It is certified that error appears in the above-identified patent and that said Letters Patent is hereby corrected as shown below:

IN THE CLAIMS
Column 17:
 Claim 1, line 61, before "formic acid" insert --hydroiodic acid, sulfuric acid, phosphoric acid, nitric acid,--.

Claim 2, line 5, in the center of the second ring of the formula, the sign should be "+", not "-".
Column 18:
 Claim 5, line 49, "maybe" should read --may be--.

Signed and Sealed this

Eighth Day of February, 1994

*Attest:*

BRUCE LEHMAN

*Attesting Officer*     *Commissioner of Patents and Trademarks*